United States Patent
Tsuge et al.

Patent Number: 5,532,376
Date of Patent: Jul. 2, 1996

[54] TRIAZOLE COMPOUNDS, THEIR INTERMEDIATES, AND METHOD FOR PRODUCTION OF THE SAME

[75] Inventors: Otohiko Tsuge, Fukuoka; Taizo Hatta, Kumamoto; Satoshi Urano, Tsuzuki-gun; Noriyuki Tsuboniwa, Osaka; Ryuzo Mizuguchi, Tokyo-to, all of Japan

[73] Assignee: Nippon Paint Co., Ltd., Osaka, Japan

[21] Appl. No.: 217,106

[22] Filed: Mar. 24, 1994

[30] Foreign Application Priority Data

Mar. 24, 1993 [JP] Japan .................... 5-065040

[51] Int. Cl.$^6$ .................... C07D 249/12
[52] U.S. Cl. .................... 548/263.2
[58] Field of Search .................... 548/263.2

[56] References Cited

U.S. PATENT DOCUMENTS 4,400,517  8/1983  Gozzo et al. .................... 548/118

FOREIGN PATENT DOCUMENTS

| | | |
|---|---|---|
| 0143613 | 11/1984 | European Pat. Off. . |
| 0556841 | 8/1993 | European Pat. Off. . |
| 50-117774 | 8/1975 | Japan . |

OTHER PUBLICATIONS

Tsuge et al, "Ring Closure Reactions of Adducts, Etc" Heterocycles, 38(2), 1994 pp. 235–241.
Journal of Organic Chemistry, vol. 41, No. 20, pp. 3233–3237. 1976; "Heterocycles from N–Ethoxycarbonylthioamides and Dinucleophilic Reagents.1.Dihydro–1,2, 4–triazolones and 1,2,4–Oxadiazolones", B. George, et al.
Tetrahedron, vol. 31, pp. 2769–2774, Pergamon Press 1975; "Spectres Photoelectroniques D'Heterocycles Carbonyles Et Thiocarbonyles"; O. Guimon et al.
Research Institute of Industrial Science, Kyushu University; Nippon Kagaku Zosshi 89, pp. 69–74, 1968; "Syntheses and Ring Closure Reactions of 1–Aryl–4–acyl–semicarbazides"; O. Tsuge, et al.
Journal of Organic Chemistry, vol. 38, No. 17, pp. 2972–2976, 1973; "Studies of Acyl and Thioacyl Isocyanates. XIII. The Reactions of Benzoyl and Thiobenzoyl Isocyanates with Hydazobenzenes and Further Investigation of the Reaction of Thiobenzoyl Isocyanate with Phenylhydrazine"; O. Tsuge et al.
Tetrahedron, vol. 24, No. 14, pp. 5205–5214, Pergamon Press 1968; "Studies of Thiobenzoyl Isocyante With Hydrazines"; O. Tsuge, et al.

*Primary Examiner*—Patricia L. Morris
*Attorney, Agent, or Firm*—Townsend & Banta

[57] ABSTRACT

The present invention relates to a triazole compound represented by the formula (1):

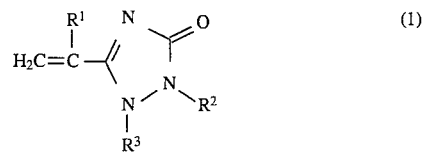

(1)

wherein $R^1$ represents a lower alkyl group which may have a substituent; $R^2$ and $R^3$ represent respectively hydrogen, an aryl group, a benzoyl group, a tosyl group, a lower alkoxy carbonyl group, or an aryl sulfonyl group, each of which except for hydrogen may have a substituent; provided that when $R^2$ is hydrogen, the triazole compound is represented by the formula (2):

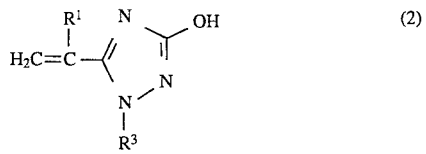

(2)

wherein $R^1$ and $R^3$ have the same as defined above.

1 Claim, No Drawings

TRIAZOLE COMPOUNDS, THEIR INTERMEDIATES, AND METHOD FOR PRODUCTION OF THE SAME

BACKGROUND OF THE INVENTION

1. Field of the Invention

The present invention relates to novel triazole compounds, their intermediates, and a method for the production of the same.

2. Description of the Prior Art

Compounds having an isocyanate group, because of their excellent reactivity, have been widely used in the area of polymer chemistry. In particular, compounds having both a polymerizable carbon-carbon unsaturated group and an isocyanate group in same molecule can be used in a wide range of industrial areas because those functional groups will participate in various reactions under different reaction mechanisms. For good utilization of such useful features, the present inventors previously proposed an acyl isocyanate compound expressed by the following formula:

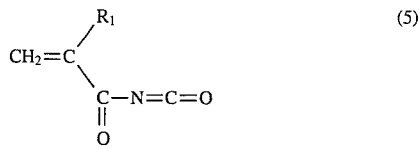

where, $R_1$ represents a lower alkyl group which may have a substituent (Japanese Patent Application Sho 58-225226).

The acyl isocyanate compound (5) is generally in the form of a liquid stable at ordinary temperatures and is easy to handle. The compound has a polymerizable carbon-carbon unsaturated group and an isocyanate group in its molecules and, in addition, it has a carbonyl group present between those two functional groups and in proximity thereto, so that not only is the activity of the carbon-carbon unsaturated group enhanced, but the activity of the isocyanate group is also enhanced and so that the compound is ready to perform a variety of addition reactions.

SUMMARY OF THE INVENTION

The object of the present invention is to provide a novel compound derived from an alkyl acryloyl isocyanate represented by the following structural formula (5):

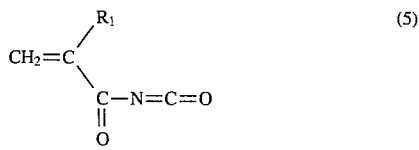

(wherein $R_1$ represents a lower alkyl group which may have a substituent group), in which the acyl isocyanate group is converted into a triazole group, with the carbon-carbon unsaturated group being retained as it is.

More specifically, the invention relates to a triazole compound represented by the formula (1):

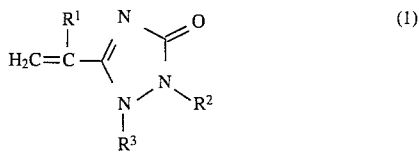

wherein $R^1$ represents a lower alkyl group which may have a substituent; $R^2$ and $R^3$ represent respectively hydrogen, an aryl group, a benzoyl group, a tosyl group, a lower alkoxy carbonyl group, or an aryl sulfonyl group, each of which except for hydrogen may have a substituent; provided that when $R^2$ is hydrogen, the triazole compound is represented by the formula (2):

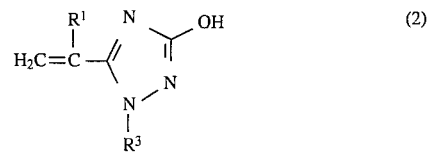

wherein $R^1$ and $R^3$ have the same as defined above.

DETAILED DESCRIPTION OF THE INVENTION

The invention relates to a triazole compound represented by the formula (1):

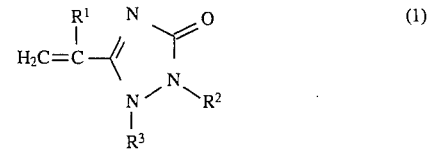

In the formula (1), $R^1$ represents a lower alkyl group, which may have a substituent. Specifically, it is an alkyl group having a carbon number of 1 to 6, such as a methyl group, an ethyl group, a butyl group, or a hexyl group.

$R^2$ and $R^3$ represent respectively hydrogen, or an aryl group, a benzoyl group, a tosyl group, a lower alkoxy carbonyl group, or an aryl sulfonyl group. Each group (except for hydrogen) represented as $R^2$ or $R^3$ may have a substituent. The aryl group is specifically one having a carbon number of 6 to 20, such as phenyl and naphthyl. The alkoxy group of the alkoxy carbonyl group has a carbon number of 1 to 8 Examples of aryl sulfonyl group are specifically phenyl sulfonyl and toluene sulfonyl (including o-, m-, p-).

The substituent which may be bonded to the group represented as $R^2$ or $R^3$ is exemplified by methyl, ethyl, propylbutyl, 2-ethyl hexyl, methoxyethyl, ethoxyethyl, butoxyethyl, hexyloxyethyl, methoxy, nitro, chloro, and bromo.

In the formula (1), when $R^2$ is hydrogen, the compound is a triazole compound expressed by the formula (2):

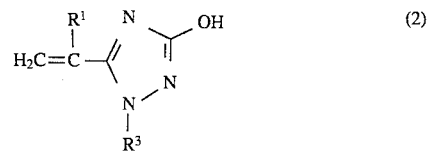

in which $R^1$ and $R^3$ are the same as above noted.

A triazole compound of the invention expressed by the formula (1) can be easily produced by heating a hydrazide compound expressed by the following formula (3):

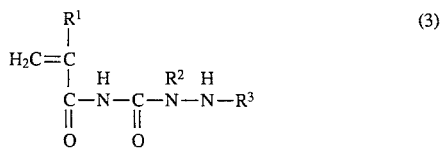

in which $R_1$, $R_2$ and $R_3$ are the same as above mentioned. The hydrazide compound (3) can be easily obtained by carrying out a reaction between an acyl isocyanate compound represented by the formula (5):

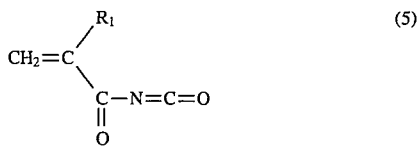

in which $R_1$ is the same as above mentioned and a hydrazine compound (6):

in which $R_2$ and $R_3$ are the same as above mentioned. It is considered that this reaction will proceed under ring formation and dehydration as illustrated:

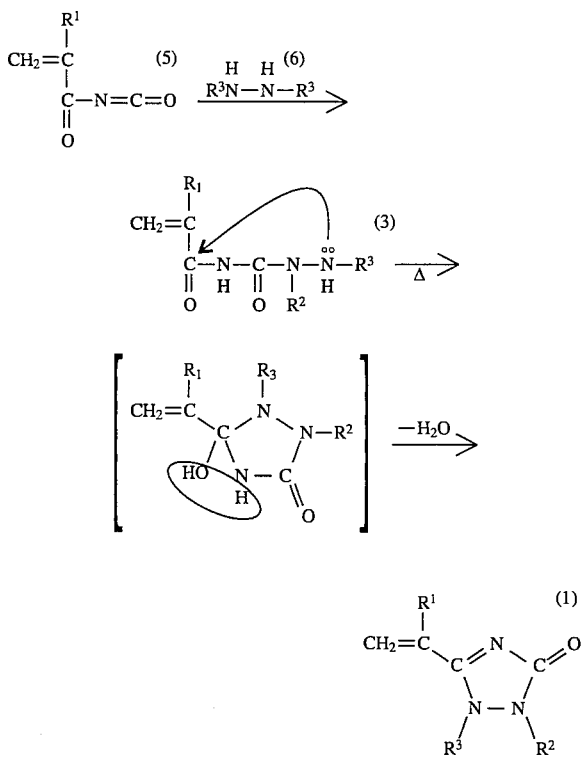

Where $R^2$ is hydrogen, a compound expressed by the formula (2) is produced by tautomerism as follows:

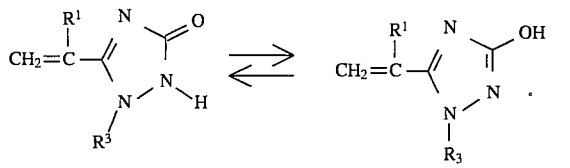

The reaction is carried out between the compound (5) and the hydrazine compound (6) of 1 to 5 equivalents in an inactive solvent at a suitable temperature within the range of −2 to 200° C. Then, an after-treatment according to a conventional method, such as concentration, and a purifying operation, such as recrystallization or column chromatography, are carried out to give a hydrazide compound (3). Generally, the compound (3) is solid and, therefore, recrystallization is most suitable for the compound (3).

Further heating of the hydrazide compound (3) will give the triazole compound (1). The compound (3) is also a novel compound.

The heating reaction above is usually carried out in an inactive solvent or an aqueous solution of potassium hydroxide. Inactive solvents useful for the purpose of the invention include, for example, aliphatic hydrocarbons, such as pentane and hexane; aromatic hydrocarbons, such as benzene, toluene, and xylene; alicyclic hydrocarbons, such as cyclohexane and cyclopentane; halogenated hydrocarbons, such as chloroform, dichloromethane, dichlorobenzene, and bromobenzene; ketones, such as acetone, methylethyl ketone, and cyclohexanone; esters, such as ethyl acetate and butyl acetate; ethers, such as diethylether, THF, dioxane, diisopropyl ether, anisole, and diphenyl ether; nitriles, such as acetonitrile and benzonitrile; amides, such as dimethylformamide and N-methylpyrrolidone; nitrobenzene; and dimethylsulfoxide. These inactive solvents may be suitably selected in consideration of heating temperature, solubility and other factors. Dehydrating agents, such as magnesium sulfide, sodium sulfide and molecular sieves, may be added to the system as required. Heating reaction is carried out at a suitable temperature within the range of room temperature to 200° C. Subsequently, concentration is effected as required, followed by purifying, to obtain a triazole compound (1) of the present invention. For purifying purposes, recrystallization is most suitable since the compound (1) is usually solid, but other conventional purifying methods, including column chromatography, may be employed.

The triazole compound (1) of the present invention, where $R^3$ is a hydrogen atom, can also be obtained by hydrolyzing the following hydrazone compound (4):

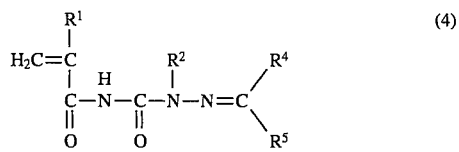

in which $R^1$ $R^2$ are the same as defined in the formula (1) $R^4$ and $R^5$ represent a lower alkyl group or an aryl group and, more specifically, include groups identical with those enumerated with respect to the previously described $R^2$ and $R^3$. The hydrazone compound (4) can be easily obtained by causing the acyl isocyanate (5) to react with the hydrazone compound expressed by the formula (7):

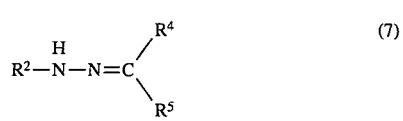

in which $R^2$, $R^4$, and $R^5$ are the same as earlier defined. This reaction is carried out under practically the same reaction conditions as those described earlier for the reaction between acyl isocyanate compound (5) and hydrazine compound (6).

The hydrazone compound (4) obtained is hydrolyzed to produce the triazole compound (1). This reaction is carried out, for example, under reflux with heating in a 10% aqueous solution of acetic acid for about 30 minutes.

This process of reaction for production of the triazole compound from the hydrazone is shown below by chemical formulas:

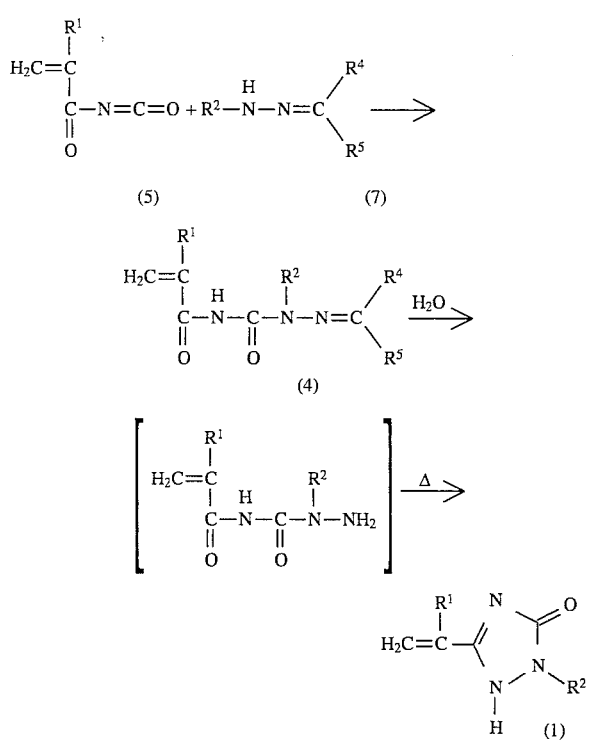

In accordance with the invention it is possible to produce the novel triazole compound (1) and intermediate compounds thereof. These new compounds are generally stable and has good storage stability and, in addition, they are in solid state, so that they are easy to purify and handle. Furthermore, these new compounds (1), (3) and (4) have various active structures and/or active groups A to C; therefore, they can participate in various reactions and accordingly can be used in a wide range of applications.

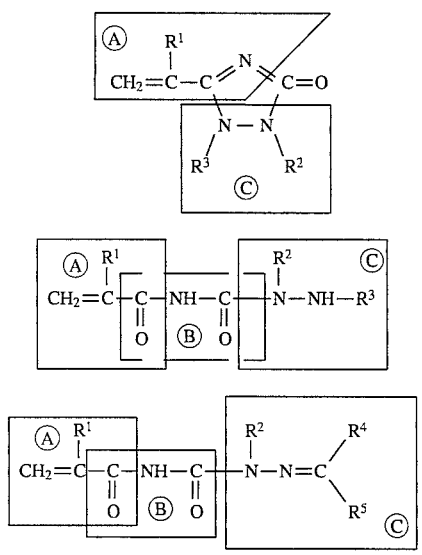

For example, in the above formulas, the structure A, which is a conjugate double bond structure, has polymerization reactivity and, therefore, the foregoing compounds (1), (3), and (4) can be used in producing homopolymers and copolymers. For example, these compounds may be graft-polymerized for use in modifying synthetic fibers, synthetic resins, natural polymers and the like. Also, they may be polymerized per se or with any other comonomer for use in producing varnishes, paints, adhesives, plastics, elastomers, etc.

The structure B, which is an acyl urethane structure or a semicarbazide bond, has high intermolecular cohesive force and high intermolecular hydrogen bond forming ability. Therefore, polymers obtained by using compounds (1), (2) and (3) can be expected to exhibit excellent performance characteristics in respect of toughness, adhesiveness and dispersibility.

The structure C, which is an amino group containing structure, is basic and can be used as a pendant for functional groups or in cross-linking of functional groups. In addition, it has high reactivity and can exhibit strong cationic characteristics when chlorinated or quaternarized. Therefore, reaction products obtained through the use of compounds (1), (3) and (4) have good water solubility and/or hydrophilic nature, good dyeability with acid dyes, and good reactivity and/or adsorptivity relative to anions. Further, such products exhibit good cohesiveness relative to negative colloids, such as sewage sludge and cellulose, have good electrical characteristics, such as electrifiability and conductivity, and also have good adhesion and dispersion properties.

In this way, the compounds (1), (3) and (4), as industrial raw materials, are useful in a wide range of applications.

It is noted that the isocyanate compound (5), as the starting material, can be produced by causing α-alkyl acryl amide with oxalyl halide.

EXAMPLES

To illustrate the invention in further detail, the following examples are given. It is understood, however, that the invention is not limited by any of these examples.

Example 1

To a THF solution (3 ml) of phenylhydrazine (1.5 g, 13.9 mmol) was added dropwise a THF solution (3 ml) of methacryloyl isocyanate (1.69 g, 15.0 mmol) at −10° C. in 40 minutes. Then, agitation was carried out at the same temperature for one hour. The precipitate was filtered to give 1.41 g of a white solid semicarbazide material. The flitrate was concentrated under reduced pressure, and the residue was recrystallized from benzene, with the result that 0.94 g of a colorless needle-like crystalline semicarbazide material was obtained. The yield was 77%. The material had a melting point of 184 to 185° C.

IR (KBr) 3294, 3228 (NH), 1678 cm$^{-1}$ (C =0).

$^1$H NMR (CDCl$_3$) δ=1.92 (3H, d, J =1.5 Hz, C$\underline{H}_3$), 5.40 (1H, q, J =1.5Hz =CH), 5.80 (1H, s, =C$\underline{H}$), 5.99 (1H, brs, N $\underline{H}$-Ph), 6.66–7.43 (5H, m, Ar$\underline{H}$), 9.04 (1H, brs, CO - N$\underline{H}$-CO), 10.04 (1H, brs, N$\underline{H}$—NHPh).

Examples 2 to 7

In the same way as in Example 1, compounds expressed by the chemical formulas shown below were prepared under the conditions shown in Table 1 below.

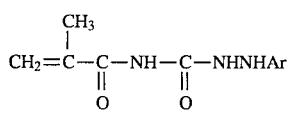

-continued

Ar: 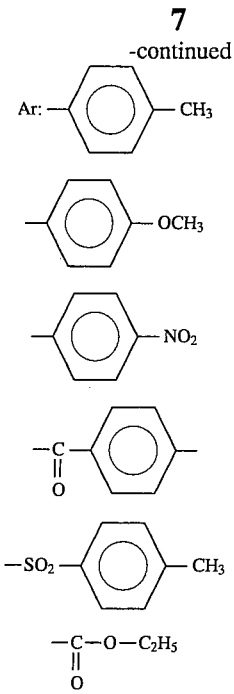

(Example 2)
(Example 3)
(Example 4)
(Example 5)
(Example 6)
(Example 7)

TABLE 1

| | Reaction Conditions | | | Product | |
|---|---|---|---|---|---|
| Example | Temp (°C.) | Solvent | Time (h) | Yield (%) | Melt point (°C.) |
| 2 | −10 | ether | 1 | 80 | 168–170 |
| 3 | 5 | benzene | 1 | 46 | 173–174 |
| 4 | −10 | THF | 1.5 | 93 | 219–220 |
| 5 | 40–45 | THF | 3 | 46 | 169–170 |
| 6 | Rm Temp. | THF | 3 | 68 | 139–140 |
| 7 | Rm Temp | benzene | 2 | 79 | 122 123 |

Examples 8 and 9

The compounds obtained in Examples 1 and 2 were refluxed in a 10% solution of potassium hydroxide. The Example 1 compound was processed for 4 hours and the Example 2 compound for 2 hours. The compounds obtained respectively had melting points of 221° to 222° C (yield: 73%) and 254° to 255° C. (yield 52%).

These compounds had the following formulas:

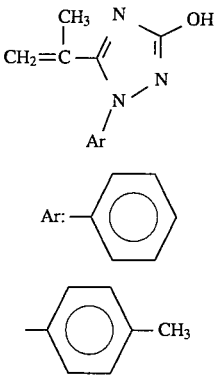

(Example 8)

(Example 9)

The IR or $^1$H NMR data for the Example 8 and 9 compounds are as follows:

IR (KBr) 2548(OH), 1576 cm$^{-1}$ (C =N). $^1$H NMR (CDCl$_3$) δ=2.00 (3H, s, C$\underline{H}_3$), 5.27, 5,33 (each 1H, s, =C$\underline{H}$), 7.37 (5H, s, Ar$\underline{H}$), 8.83 (1H, s, O$\underline{H}$). IR (KBr) 2588 (OH), 1578 cm=1 (C =N).

Examples 10 and 11

The compounds obtained in Examples 1 and 2 were refluxed in m-xylene under the conditions shown in Table 2. After cooling, the solvent was distilled away and each of the compounds was recrystallized from ethanol to give a product. The products were obtained in such yields and had such melting points as shown in Table 2.

TABLE 2

| | Reaction Conditions | | Product | |
|---|---|---|---|---|
| Example | Temperature | Time(h) | Yield (%) | Melt point (°C.) |
| 10 | Reflux | 12 | 76 | 173–174 |
| 11 | Reflux | 12 | 22 | 187–188 |

It is presumed that these compounds have the following chemical formulas.

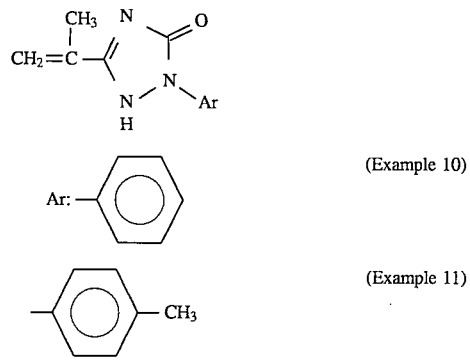

(Example 10)

(Example 11)

Examples 12 to 14

Methacryloyl isocyanate was caused to react with each of the hydrazone compounds expressed by the following formulas:

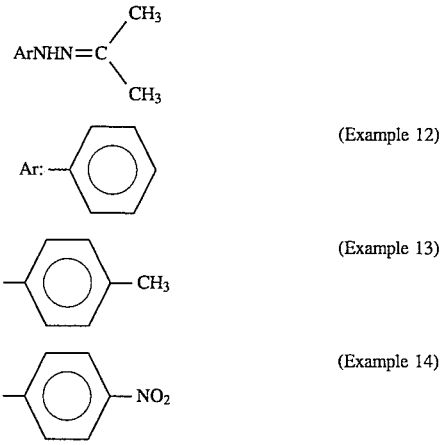

(Example 12)

(Example 13)

(Example 14)

TABLE 3

| Example | Reaction Conditions | | | Product | |
|---|---|---|---|---|---|
| | Temp (°C.) | Solvent | Time (h) | Yield (%) | Melt point (°C.) |
| 12 | −15—−13 | ether | 2 | 86 | 144–145 |
| 13 | Rm Temp. | ether | 5 | 57 | 117–118 |
| 14 | Reflux | THF | 2 | 27 | 139–140 |

The IR and $^1$H NMR data for the Example 12 compound are as follows:

IR (KBr) 3320, 3224 (NH), 1736 cm$^{-1}$ (C =0). $^1$H NMR (CDCl3) δ=1.70 (6H, s, N =C (C$\underline{H}_3$)$_2$), 2.07 (3H, s, C$\underline{H}$ $_3$) 4.60 (1H, brs, =N$\underline{H}$), 5.43 (2H, s, =C$\underline{H}$), 6.90–7.50 (3H, m, Ar$\underline{H}$), 7.60–7.93 (2H, m, Ar$\underline{H}$).

The compound obtained was heated in a 10% acetic acid solution. The resulting product had the following formula.

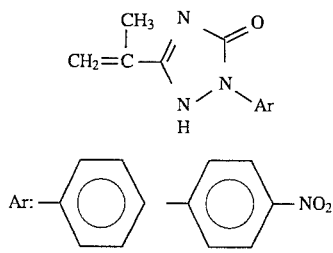

What is claimed is:

1. A triazole compound represented by the formula (1)

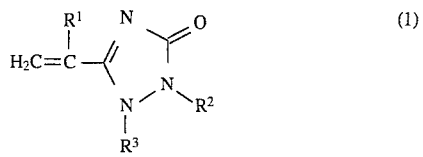

wherein R$^1$ represents a lower alkyl group which may have a substituent selected from the group consisting of an alkyl group having 1–6 carbon atoms; R$^2$ and R$^3$ respectively hydrogen, an aryl group, having 6–20 carbon atoms, a benzoyl group, a tosyl group, a lower alkoxy carbonyl group, or an aryl group having 6–20 carbon atoms and substituted with sulfonyl guoup, each of which except for hydrogen may have a substituent selected from the group consisting of methyl, ethyl, propylbutyl, 2-ethyl hexyl, methoxyethyl, ethoxyethyl, butoxyethyl, hexyloxyethyl, methoxy nitro, chloro and bromo provided that when R$^2$ is hydrogen, the triazole compound is represented by the formula (2):

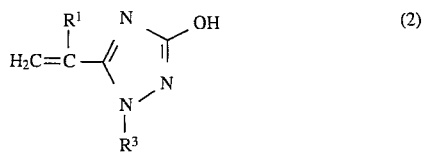

wherein R$^1$ and R$^3$ have the same as defined above.

* * * * *